United States Patent [19]

Greco et al.

[11] Patent Number: 4,888,375
[45] Date of Patent: Dec. 19, 1989

[54] ORGANIC POLYMER STABILIZATION

[75] Inventors: Alberto Greco; Luigi Cassar; Silvestro Costanzi; Carlo Neri, all of Milan, Italy

[73] Assignee: Enichem Sintesi S.p.A., Palermo, Italy

[21] Appl. No.: 101,638

[22] Filed: Sep. 28, 1987

Related U.S. Application Data

[62] Division of Ser. No. 733,524, May 13, 1985, abandoned.

[30] Foreign Application Priority Data

May 21, 1984 [IT] Italy .................... 21024 A/84

[51] Int. Cl.$^4$ ............................ C08K 5/24; C08K 5/54
[52] U.S. Cl. .................................. 524/262; 524/261; 524/265; 524/268; 524/269
[58] Field of Search ................ 524/262, 265, 268, 269, 524/261

[56] References Cited

U.S. PATENT DOCUMENTS

| | | | |
|---|---|---|---|
| 4,582,870 | 4/1986 | Spivack et al. | 524/262 |
| 4,636,573 | 1/1987 | Pastor et al. | 524/261 |
| 4,818,779 | 4/1989 | Witucki et al. | 524/262 X |

*Primary Examiner*—Paul F. Shaver
*Attorney, Agent, or Firm*—Hedman, Gibson, Costigan & Hoare

[57] ABSTRACT

Reactive antioxidant compounds, able to stabilize organic polymers, contain in their molecule a sterically hindered phenolic group and a hydrolysable silyl function. In stabilizing organic polymers, said reactive antioxidant compounds can be hydrolysed at the silyl function with the formation of silanol groups, which are made to interact in order to form complex resinous stabilizing structures. These latter are added in stabilizing quantities to the polymer to be stabilized. According to one particular embodiment, the hydrolysis at the silyl function and the formation of the resinous structure take place spontaneously within the polymer to be stabilized. According to a further embodiment, the reactive antioxidant compound is added to the polymer after being stably supported on a solid support by reaction with an inorganic solid having surface hydroxyl groups. According to a further embodiment, the reactive antioxidant compound is made to interact with the polymer so that the stabilizing compound becomes chemically bonded to the polymer chains. In all cases, stabilized polymers are obtained containing the antioxidant compound in a form which is not removable from the polymer. The processes for preparing the reactive antioxidant compounds and for preparing the stabilized polymer compositions are also described.

24 Claims, No Drawings

ORGANIC POLYMER STABILIZATION

This is a division of application Ser. No. 733,524, filed May 13, 1985, now abandoned.

This invention relates to reactive antioxidant compounds able to stabilise organic polymers, and also relates to the polymer compositions stabilised by said antioxidant compounds and the processes for preparing said antioxidant compounds and said stabilised polymer compositions. Organic polymers are known to suffer degradation with the passage of time due to exposure to the environmental conditions, and this degradation manifests itself as a worsening of the polymer physical characteristics, such as a reduction in the ultimate tensile stress and flexibility, these being accompanied by a change in the viscosity index. In order to oppose this degradation, it is usual in industry to introduce small quantities of antioxidant compounds, generally in the form of sterically hindered phenols, into the polymers. The problems encountered in the stabilisation of organic polymers derive essentially from incompatibility between the antioxidant and the polymer, and from the release of the antioxidant by the polymer. In stabilisation by means of known antioxidants, these undesirable phenomena are always manifested, whether at a greater or lesser level, and there is therefore a need for antioxidant compounds having greater compatibility with the polymers and able to permanently remain therein. It has now been found that such a requirement can be satisfied by the reactive antioxidant compounds of the present invention, which contain in their molecule a sterically hindered phenolic group and a hydrolysable silyl function.

These reactive antioxidant compounds can give rise to complex resinous structures either within the polymer or outside it, or can bond chemically to the polymer or to a solid support. The results of these interactions is that structures are obrained which on the one hand unexpectedly preserve the inherent stabilising characteristics of the sterically hindered phenols, and on the other hand present characteristics of compatibility with and permanence in the polymer which exceed those of the initial reactive antioxidant compounds and those of antioxidants known in the art. Accordingly, one object of the present invention is constituted by reactive antioxidant compounds containing in their molecule a sterically hindered phenolic group and a hydrolysable silyl group. A further object of the present invention is constituted by processes for preparing said reactive antioxidant compounds. A further object of the present invention is constituted by polymer compositions stabilised by the products of the transformation of said reactive antioxidant compounds at the silyl function. A further object of the present invention is constituted by processes for preparing said stabilised polymer compositions. Further objects of the invention will be apparent from the description and experimental examples given hereinafter. In general, the reactive antioxidant compounds of the present invention are compounds containing the sterically hindered phenolic group:

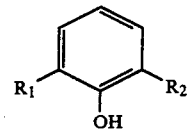
(I)

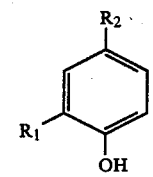
(Ia)

where $R_1$ and $R_2$, which can be equal or different, are preferably branched alkyl radicals containing from 1 to 10 carbon atoms, and in their most preferred form are tert-butyl radicals; said phenolic groups (I) and (Ia) carrying a silyl function hydrolysable to silanol and connected to the ring by a silicon-carbon bond. More particularly, the reactive antioxidant compounds of the present invention can pertain to the following class of compounds:

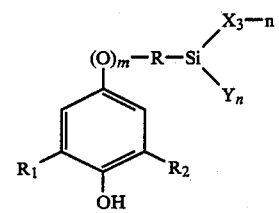
(II)

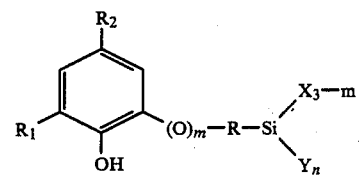
(IIa)

where $R_1$ and $R_2$ are as heretofore defined;
m is zero or one;
R is a linear or branched alkylene radical containing from 1 to 10 carbon atoms, or can be defined by means of

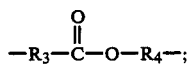

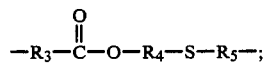

(where $R_3$, $R_4$ and $R_5$ are linear or branched alkylene radicals containing a total of between 3 and 10 carbon atoms);
X is a linear or branched alkyl radical containing from 1 to 5 carbon atoms, and preferably the methyl radical;
Y is hydrogen, halogen and preferably chlorine, $C_1$–$C_4$ acyloxy, $C_1$–$C_4$ alkyloxy, amino, amino-oxy or silyloxy, and preferably $C_1$–$C_2$ alkyloxy;
n is one, two or three.

Specific examples of reactive antioxidant compounds which fall within formula (II) are the following:

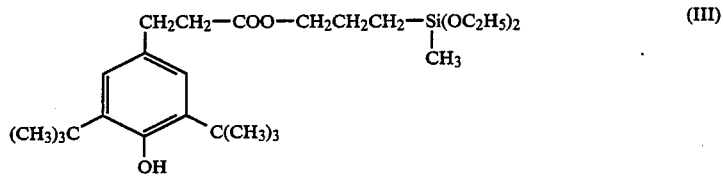 (III)

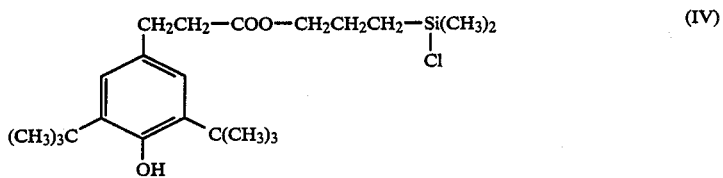 (IV)

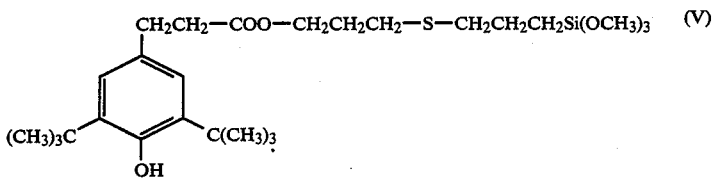 (V)

The reactive antioxidant compounds (III), (IV) and (V) can be obtained from the compound:

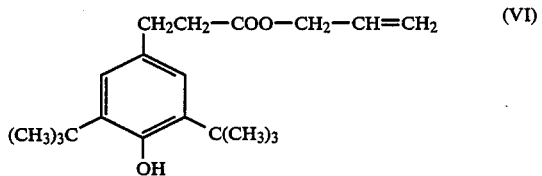 (VI)

by silylation with methyldiethoxysilane, dimethylchlorosilane and γ-mercaptopropyltrimethoxysilane respectively. A further specific example of a reactive antioxidant compound falling within formula (II) is the following:

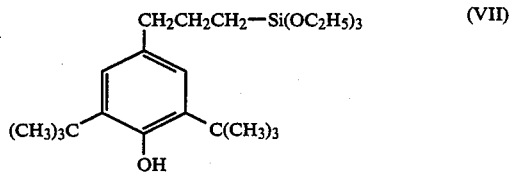 (VII)

The reactive antioxidant compound (VII) can be obtained by silylation of the compound:

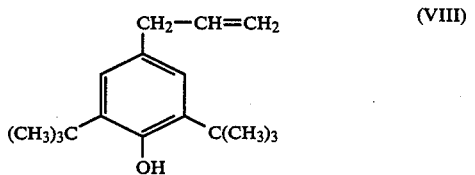 (VIII)

with triethoxysilane.

A further example of a reactive antioxidant compound falling within general formula (II) is the following:

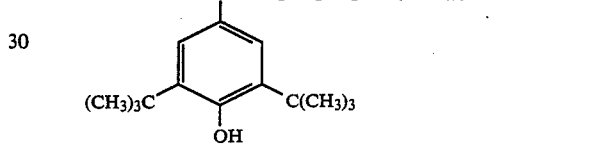 (VIIIa)

The reactive antioxidant compound (VIIIa) can be obtained by silylation with trimethoxysilane of the compound:

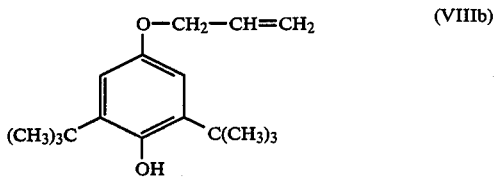 (VIIIb)

In general the reactive antioxidant compounds of the present invention can be prepared by silylating a sterically hindered phenol carrying on its ring a preferably terminal ethylenically unsaturated group.

One class of silylation agents suitable for this purpose is definable by the formula:

 (IX)

A further class of silylation agents suitable for the purpose is definable by the general formula:

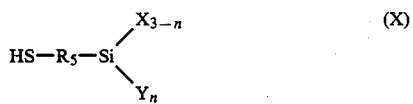 (X)

where $R_5$, X, Y and n have the aforesaid meanings.

Specific examples of silylation agents falling within general formula (IX) are:

HIS(CH$_3$)$_2$Cl; HSI(CH$_3$)Cl$_2$; HSiCl$_3$;
HSi(O-CH$_3$)$_2$(CH$_3$); HSi(CH$_3$)(O-C$_2$H$_5$)$_2$;
HSi(O-C$_2$H$_5$)$_3$; H$_2$Si(C$_2$H$_5$)$_2$;
HSi(OCH$_3$)$_3$; HSi(CH$_3$)$_2$-O-Si(CH$_3$)$_2$H;
HSi(CH$_3$)$_2$-O-Si(CH$_3$)(OCH$_3$)$_2$;
HSi(CH$_3$)$_2$ONC(CH$_3$)$_2$;
HSi(CH$_3$)[ONC(CH$_3$)$_2$]$_2$

Specific examples of silylation agents which fall within general formula (X) are γ-mercaptopropyltrialkoxysilanes and in particular γ-mercaptopropyltrimethoxysilane.

The silylation reaction is conveniently conducted at a temperature of between 0° and 200° C., and preferably between ambient temperature (20°-25° C.) and 120° C., with a reagent quantity varying from stoichiometric to an excess of the silylation reagent. Said excess usually reaches up to 20% on a molar basis. However, if disilanes are used it is convenient to use a large excess of the silylation agent, for example up to about 10 times the stoichiometric quantity. The silylation reaction is catalysed by metal catalysts, by ultraviolet radiation and by radical initiators. THe preferred catalysts are platinum compounds and complexes of platinum with olefins, in particular chloroplatinic acid. In the case of platinum catalysts, the catalyst concentration, evaluated as metal, can vary from 1 to 200 parts per million and preferably from 5 to 50 parts per million in the reaction medium.

The silylation reaction can be conducted in an inert (unreactive) organic solvent, normally chosen from aliphatic, cycloalpihatic and aromatic hydrocarbons and ethers, which are liquid under the operating conditions. Specific examples of solvents suitable for this pupose are heptane, cyclohexane, toluene, tetrahydrofuran, dioxane and dimethoxyethane. The reaction times depend on the particular reagents used and the reaction temperature, and vary normally from 0.5 to 10 hours. On termination of the silylation reaction, any solvent used and any excess silylation agent are removed by stripping, and the reactive stabillising compound is recovered from the residue of said stripping by normal methods such as crystallisation and distillation under vacuum. However, generally the high yield and selectivity of the silylation reaction make any separation or purification of the final required product unnecessary. If silylating compounds falling within formula (X) are used, the reaction is conveniently conducted under the aforesaid general silylation conditions with catalysts in the form of azo compounds such as azobisisobutyronitrile, which are used in a quantity of between 0.1% and 10% and preferably between 0.5% and 2% in the reaction environment. The reactive antioxidant compounds of the present invention hydrolyse at the silyl function under mild conditions, to generate silanol groups which can be condensed together to form complex resinous stabilising structures. These resinous structures, of silicone resin type, preserve the inherent stabilising characteristics of sterically hindered phenols, and have a high level of compatibility with organic polymers, and practically no extractability from said polymers. Hydrolysis at the silyl function takes place simply by contact with water or with environmental moisture at ambient temperature (20°-25° C.) or lower than ambient. Condensation between the silanol groups to give the complex resinous structures can be facilitated by acid or basic agents, soaps or metal esters, and organometal compounds, especiallly of lead and tin. Preferred catalysts for this purpose are lead naphthenate and tin dibutyl-laurate. Conveniently, the catalyst quantity can vary from 0.1% to 10% by weight and preferably from 0.2% to 3% by weight with respect to the reactive antioxidant compound subjected to resinification. Said resinification reaction can be conducted at ambient temperature (20°-25° C.) or at higher or lower than ambient. The complex resinous structures thus obtained can be introduced into the organic polymer to be stabilised by the usual methods used for this purpose. According to a further embodiment of the present invention, the reactive antioxidant compounds are introduced directly into the organic polymer, within which the hydrolysis reaction at the silyl function and the interaction between the silanol groups take place spontaneously, to thus give the stabilised polymer composition. According to a further embodiment, hydrolysis at the silyl function o the reactive antioxidant compounds takes place externally to the polymer, together with partial resinification of the hydrolysis products thus obtained. The product of the partial resinification is then introduced into the organic polymer to be stabilised, within which complete resinification takes place. According to a further embodiment, the reactive antioxidant compounds of the present invention are co-resinified with conventional silicone varnishes. Generally, the co-resinification requires baking at relatively high temperaure. The materials thus obtained are complex resins in which the antioxidant is one of the constituent elements. These materials are generally hard, transparent glasses which can be ground to give a powder with an average particle size of 1 micron or less. In this form, the antioxidant can be distributed and homogenised in the polymer to be stabilised, in pigment form. The structure of these resinification products depends essentially on the number of groups hydrolysable at the silyl function in the reactive antioxidant compounds. For example in the case of compound (IV), which contains only one hydrolysable group, the hydrolysis and resinification reactions proceed until a dimer is produced, which in the case in question can be defined by the following general formula:

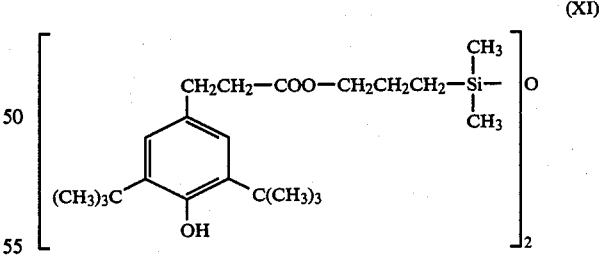

(XI)

In the case of reactive antioxidant compounds which contain more than on hydrolysable group in the silyl function, more complex resinification products are obtained.

The reactive antioxidant compounds of the present invention can be fixed to a solid support containing surface hydroxyl groups. Supports suitable for this purpose are siliceous materials, of either natural or synthetic origin, such as diatomaceous earth, celite, silica gel, cement, glass/flass fibres and silico-aluminates in general. The preferred of all these supports is that type of silica commonly known as fumed silica which, together with good optical characteristics, has low apparent density, a high specific surface (generally exceeding 200 m²/g) and a high surface concentration of hydroxyl groups. The bond to the support is produced by reacting the reactive antioxidant compound in its hydrolysed form with the surface hydroxyl groups of the support. In practice, the support, in the form of powder or granules, is brought into contact with a solution of the reactive antioxidant compound in an inert solvent, such as an aliphatic, cylcoaliphatic or aromatic hydrocarbon or an ether. The procedure is carried out in the liquid phase at a temperature of between ambient (20°-25° C.) and about 100° C. The reactive antioxidant compound becomes hydrolysed and bonded to the support within a time of the order of between 0.4 and 10 hours. The stabilizing compound thus supported is added to the organic polymer to be stabilised, by normal methods. This embodiment has the further advantage of excellent distribution of the antioxidant in the polymer.

According to a further embodiment, the reactive antioxidant compounds of the present invention are bonded chemically to the organic polymer to be stabilised. This method is particularly effective in the case of diolefinic polymers and copolymers of low molecular weight. The reaction between the reactive antioxidant compound and the polymer generally takes place at a temperature of between ambient (20°-25° C.) and about 100° C., in the presence of an inert (unreactive) diluent, in a time of between 0.5 and 10 hours. The reactive antioxidant compounds of the present invention are able to stabilise organic polymers in general, such as polyolefins, including polyethylene, polypropylene, polyisobutene and ethylene-propylene copolymers, polydiolefins including polybutadiene and polyisoprene, and polyethers, including polyethyleneoxide and polypropyleneoxide. The stabilised polymer compostions of the present invention contain a stabilising quantity of the antioxidant compound, the term "stabilising quantity" signifying that quantity which adds from 0.01% to 5% by weight of phenolic antioxidant. The following experimental examples are given for illustrative purposes, and do not limit the range of the invention.

EXAMPLE 1

Preparation of the compound (III):

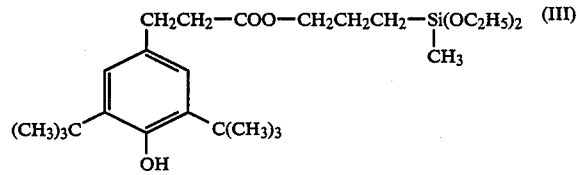

The compound (VI)

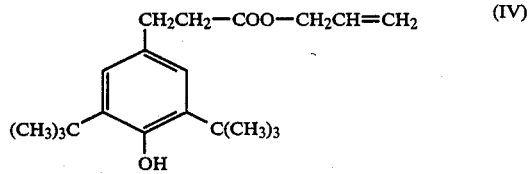

which is a slightly yellow solid with a melting point of 36°-37° C. and obtained by esterifying the corresponding acid with allyl alcohol (5.0 g; 18.0 mmoles), is reacted in toluene (5 ml) with methyldiethoxysilane (4.1 ml; 3.4 g; 25.0 mmoles) in the presence of traces of chloroplatinic acid dissolved in isopropanol (10 μl of a 2 weight % solution of $H_2PtCl_6.6H_2O$), operating firstly at ambient temperature (the reaction is slightly exothermic) and then at 80° C. for 4 hours.

The completeness of the reaction is indicated by the disappearance of the IR band at 1650 cm$^{-1}$ (allyl unsaturation). The reaction product thus obtained is subjected to fractional distillation under reduced pressure (1 torr) in a bulb still to give 5.9 g of a slightly straw-coloured oil [yield 73% with respect to compound (VI)], which distils at a boiler temperatue of 240° C. (1 torr) and is constituted by the compound (III).

Elementary analysis: theoretical: C: 66.4%, H: 9.7%, found: C: 66.7%, H: 9.7%.

The mass spectrum (M+452) and IR and $^1$Hnmr analysis confirm the aforesaid structure.

EXAMPLE 2

Preparation of the compound (IV):

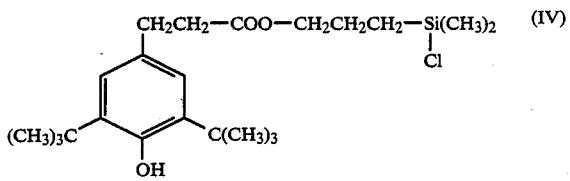

The compound (VI) (3.5 g; 11.0 mmoles) is reacted with dimethylchlorosilane (1.45 ml; 1.2 g; 13.0 mmoles) under the conditions of Example 1. The reaction product is stripped, and a residue remains consisting of 4.5 g of the compound (IV) (yield practically total).

Elementary analsysi: theoretical: C: 64.0%, H: 9,0%, Cl: 8.6%, found: C: 64.3%, H: 8.9%, Cl: 7.9%.

The mass spectrum (M+412) and IR and $^1$Hnmr analysis confirm the aforesaid structure.

EXAMPLE 3

Preparation of the compound (IX):

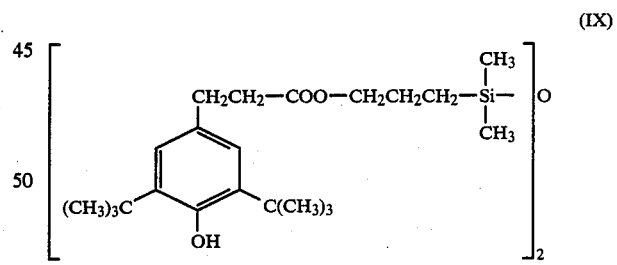

by hydrolysis and resinification of the compound (IV).

The compound (IV) (2.5 g; 6.1 mmoles) of the preceding Example 2 is dissolved in 15 ml of diethyl ether and hydrolysed by adding about 5 g of ice, which makes contact therewith. After liquefaction of the ice, the aqueous and organic phases are agitated for 2 hours at ambient temperature. The ether layer is then separated, washed with aqueous sodium bicarbonate and water and dried under vacuum, with the elimination of the diethyl ether. 2.15 g (yield practically total) are thus obtained of a viscous oil constituting the compound (IX).

Elementary analysis: theoretical: C: 68.6%, H: 9.6%. found: C: 67.9%, H: 9.5%.

The mass spectrum does not produce the parent ion. IR and $^1$Hnmr analysis confirm the aforesaid structure.

EXAMPLE 4

Preparation of the compound (V):

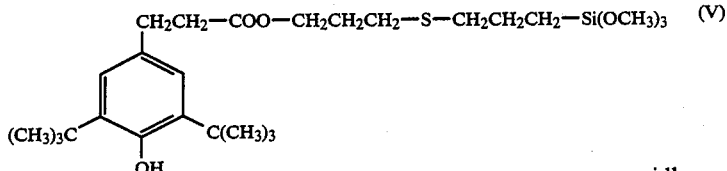

The compound (VI) (4.1 g; 14.8 mmoles) is reacted with γ-mercaptopropyltrimethoxysilane (3.7 g; 3.5 ml; 19.0 mmoles) and with azobisiisobutyronitrile (130 mg) dissolved in 4 ml of toluene, operating in a flask fitted with a magnetic agitator. The solution is agitated for 4 hours at 85° C. and is then heated to 110° C. and kept at this temperature for one hour. The reaction product thus obtained is a slightly straw-coloured oil which after stripping under reduced pressure cannot be further distilled with a boiler temperature of 240° C. The stripping residue [4.8 g; yield 63% with respect to the compound (VI)]is constituted by the required compound (V).

Elementary analysis: theoretical: C: 60.7%, H: 8.9%, S: 6.2%. found: C: 59.3%, H: 8.8%, S: 6.5%.

The mass spectrum (M+514) and IR and $^1$Hnmr analysis confirm the aforesaid structure.

EXAMPLE 5

Grafting of the compound (IV) onto metal-treated polybutadiene. A low-molecular weight liquid polybutadiene is prepared by polymerising 1,3 butadiene (10.8 g; 200 mmoles) dissolved in cyclohexane (150 ml), with n-butyllithium (hydrocarbon solution; 10 mmoles) in a bottle. The reaction is conducted at 50° C. until complete conversion of the butadiene to polybutadiene (average molecular weight 1080) is obtained, wtih Li termination. The botle is cooled to ambient temperature, and the compound (IV) (2.1 g; 5 mmoles) is cautiously added to the bottle, which is occasionally shaken. After 2 hours at ambient temperature, 5 ml of methanol are added, the organic phase is washed with aqueous hydrochloric acid and then with water, and the washed organic phase is stripped, to obtain a residue of 12 g of polybutadiene to which the compound (IV) is bonded.

EXAMPLE 6

The stabilising action of the antioxidants of the present invention is verified in a laboratory test under conditions suitable for accelerating the thermal degradation of the polypropylene. Polypropylene films containing the stabiliser are subjected to prolonged heat treatment in an air circulation oven at 130° C. The progress of the degradation is verified by the formation of carbonyl compounds, which are demonstrated by IR spectra. Specifically, the carbonyl index ($I_{co}$) is calculated from the relationship [100×(intensity of the band at 1720 $cm^{-1}$-base intensity at 1850 $cm^{-1}$)/ film thickness in μm]. The longer the induction time for the formation of the carbonyl compounds, the more effective is the stabilising effect. The film containing the stabiliser is prepared by dissolving the antioxidant in benzene and mixing the solution thus obtained with powdered polypropylene. The polypropylene is free from any other additive. The solvent is evaporated under reduced pressure, and the film is then prepared with a thickness of about 100 μm, by pressing at a temperature of 150° C. under a pressure of 900 kg/cm$^2$ for a time of 2 minutes. The film is extracted from the press and rapidly cooled under running water. For the stabilisation tests, the compound (IX) is used prepared in accordance with Example 3, in a quantity of 0.7% by weight with respect to the polypropylene. For comparison purposes, the polypropylene is also stabilised with the commercial antioxidants IRGANOX 1010 and IRGANOX 1076 used in quantities such as to add the same quantity of phenolic hydroxyls as the compound (IX). The results of these tests are given in the following Table 1.

TABLE 1

| Stabiliser | Induction time (minutes) |
| --- | --- |
| None | <180 |
| IRGANOX 1010 | >11000 |
| IRGANOX 1076 | >11000 |
| COMPOUND (XI) | >11000 |

We claim:
1. Stabilized polymer compositions comprising an organic polymer and a stabilizing quantity of a reactive antioxidant compound having the formula

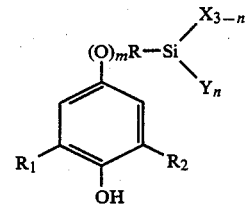

or the formula

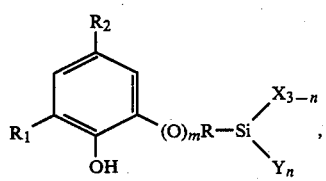

wherein $R_1$ and $R_2$ are linear or branched alkyl radicals containing from 1 to 10 carbon atoms;

R is a linear or branched alkylene radical containing from 1 to 10 carbon atoms, or is

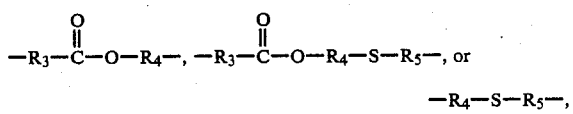

wherein $R_3$, $R_4$ and $R_5$ are linear or branched alkylene radicals containing 3 to 10 carbon atoms;

X is a linear or branched alkyl radical containing form 1 to 5 carbon atoms;

Y is hydrogen, halogen, $C_1$-$C_4$ acyloxy, $C_1$-$C_4$ alkyloxy, amino, amino-xoy, or silyloxy;

m is zero or 1; and n is 1, 2 or 3.

2. Stabilized polymer compositions comprising an organic polymer and a stabilizing quantity of a resinified antioxidant comprising the hydrolysis and condensation product of a compound having the formula

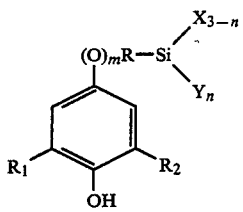

or the formula

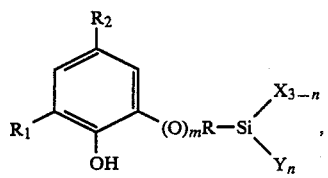

wherein $R_1$ and $R_2$ are linear or branched alkyl radicals containing from 1 to 10 carbon atoms;

R is a linear or branched alkylene radical containing from 1 to 10 carbon atoms, or is

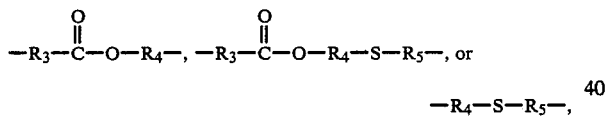

wherein $R_3$, $R_4$ and $R_5$ are linear or branched alkylene radicals containing 3 to 10 arbon atoms;

X is a linear or branched alkyl radical containing from 1 to 5 carbon atoms;

Y is hydrogen, halogen, $C_1$-$C_4$ acyloxy, $C_1$-$C_4$ alkyloxy, amino, amino-xoy, or silyloxy;

m is zero or 1; and n is 1, 2 or 3.

3. Stabilized polymer compositions as defined in claim 2, wherein, in said phenolic compound, $R_1$ $R_2$ are t-butyl, X is methyl, and Y is chlorine, methoxy or ethoxy.

4. Stabilized polymer compositions as defined in claim 2, wherein said phenolic compound is selected from the group consisting of

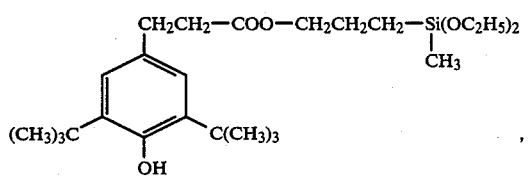

-continued

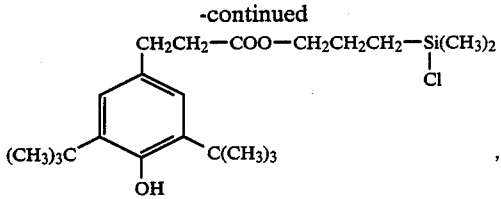

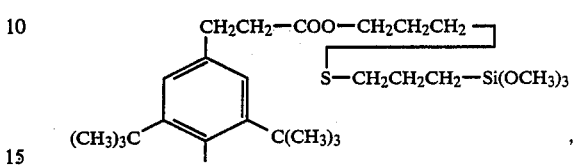

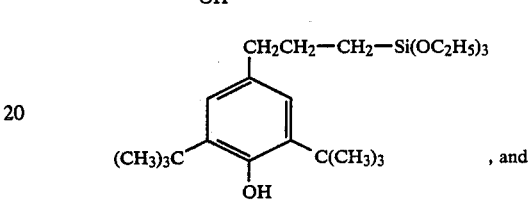

, and

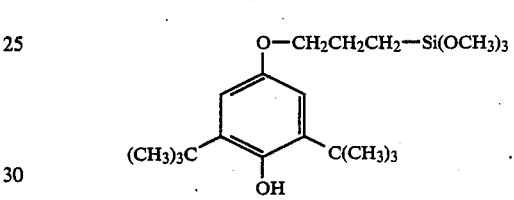

5. Stabilized polymer compositions as defined in claim 4, wherein said resinified antioxidant has the formula:

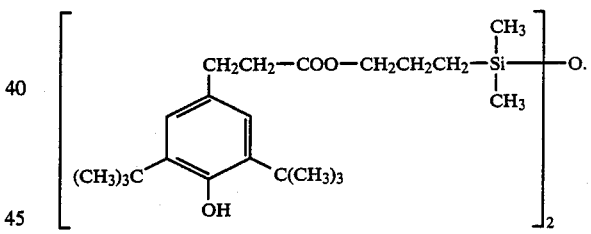

6. Stabilized polymer compositions as defined in claim 2, wherein said phenolic organic polymer is a polyolefin, a polydiolefin, or a polyether.

7. Stabilized polymer compositions as defined in claim 2, wherein said compound is resinified in the presence of said organic polymer.

8. Stabilized polymer compositions as defined in claim 2, wherein said compound is at least partially resinified before combination with said organic polymer.

9. Stabilized polymer compositions as defined in claim 2, wherein said resinified antioxidant is a granulated co-resinification product of said compound and a silicone varnish.

10. Stabilized polymer compositions as defined in claim 1, wherein said organic polymer is a polyolefin, a polydiolefin, or a polyether.

11. Stabilized polyme compositions as defined in claim 1, wherein said reactive antioxidant compound is fixed to a solid support containing surface hydroxyl groups, selected from diatomaceous earth, celite, silica gel, cement, glass, glass fibres, silico-aluminates or fumed silica.

12. Stabilized polymer compositions as defined in claim 1, wherein said reactive antioxidant compound is present in an amount 0.01% to 5% by weight.

13. Stabilized polymer compositions as defined in claim 2, wherein said resinified antioxidant is present in an amount of from 0.01% to 5% by weight.

14. A process for stabilizing oganic polymers comprising:
incorporating in said polymer 0.01% to 5% by weight of a phenolic antioxidant, said antioxidant having the formula

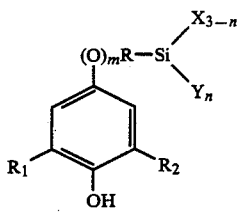

of the formula

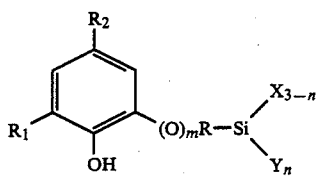

wherein $R_1$ and $R_2$ are linear or branched alkyl radicals containing from 1 to 10 carbon atoms;
R is a linear or branched alkylene radical containing from 1 to 10 carbon atoms, or is

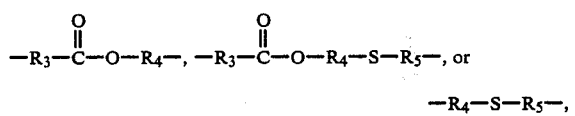

wherein $R_3$, $R_4$ and $R_5$ are linear or branched alkylene radicals having 3 to 10 carbon atoms;
X is a linear or branched alkyl radial containing from 1 to 5 carbon atoms;
Y is hydrogen, halogen, $C_1$-$C_4$ acyloxy, $C_1$-$C_4$ alkyloxy, amino, amino-oxy, or silyloxy;
m is zero or 1; and
n is 1, 2 or 3;
such that said antioxidant is inextractable from said polymer.

15. The process according to claim 14, wherein said antioxidant is incorporated into said polymer under conditions which cause the hydrolysis of the silyl function of said antioxidant and condensation to form inextractable, resinous products within the organic polymer.

16. The process according to claim 15, wherein said hydrolysis and condensation are carried out in the presence of a condensation catalyst selected from acid or basic agents, metal soaps, metal esters, or organo-metal compounds.

17. The process according to claim 16, wherein said condensation catalyst is lead naphthenate or tin dibutyllaurate.

18. The process according to claim 14, wherein the incorporation step involves partially resinifying said phenolic antioxidant prior to combination with the organic polymer and thereafter combining the partially resinified compound with the organic polymer under conditions which cause the further resinification of said compound to form inextractable, resinous structures within said polymer.

19. The process according to claim 18, wherein said hydrolysis and condensation are carried out in the presence of a condensation catalyst selected from acid or basic agents, metal soaps, metal esters, or organo-metal compouns.

20. The process according to claim 19, wherein said condensation catalyst is lead naphthenate or tin dibutyllaurate.

21. The process according to claim 14, wherein the incorporation step involves reacting said antioxidant with a solid support containing surface hydroxyl groups selected from the group consisting of diatomaceous earth, celite, silica gel, cement, glass, glass fibers, silico-aluminates and fumed silica; or, optionally.

22. The process according to claim 14, wherein the incorporation step involves co-resinifying said antioxidant compound with a silicone varnish to obtain a hard glass, particulating said glass to an average particle size of 1 micron or less, and adding said particulate glass to said organic polymer.

23. The process according to claim 14, wherein the incorporation step involves bonding chemically said antioxidant to said polymer.

24. The process according to claim 14, wherein said organic polymer is a polyolefin, a polydiolefin, or a polyether.

* * * * *